(12) United States Patent
Adams et al.

(10) Patent No.: US 6,482,606 B1
(45) Date of Patent: *Nov. 19, 2002

(54) HUMAN DNA MISMATCH REPAIR POLYNUCLEOTIDES

(75) Inventors: Mark D. Adams, North Potomac, MD (US); Robert D. Fleischmann, Washington, DC (US); Claire M. Fraser, Queenstown, MD (US); Rebecca A. Fuldner, Barnesville, MD (US); Ewen F. Kirkness, Washington, DC (US); William A. Haseltine, Washington, DC (US); Craig A. Rosen, Laytonsville, MD (US); Steve Ruben, Olney, MD (US); Ying-Fei Wei, Darnestown, MD (US)

(73) Assignee: Human Genome Sciences, Inc., Rockville, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/187,757

(22) Filed: Jan. 27, 1994

(51) Int. Cl.⁷ ............... C12P 21/02; C12N 1/00; C12N 1/20; C12N 5/10
(52) U.S. Cl. ............. 435/69.1; 435/71.1; 435/71.2; 435/243; 435/252.3; 435/320.1; 435/325; 435/410; 536/23.1; 536/23.2; 536/23.5
(58) Field of Search ............... 536/23.1, 23.2, 536/23.5; 435/320.1, 325, 410, 243, 69.1, 71.1, 71.2, 252.3

(56) References Cited

U.S. PATENT DOCUMENTS

| | | | |
|---|---|---|---|
| 4,737,454 A | | 4/1988 | Dattagupta et al. |
| 5,124,443 A | * | 6/1992 | Colella et al. ............ 536/23.2 |
| 5,922,855 A | | 7/1999 | Liskay et al. |
| 6,165,713 A | | 12/2000 | Liskay et al. |
| 6,191,268 B1 | * | 2/2001 | Liskay et al. ............ 536/23.5 |

FOREIGN PATENT DOCUMENTS

| | | |
|---|---|---|
| WO | WO 95/14772 | 11/1993 |
| WO | WO 95/16793 | 12/1994 |
| WO | WO 95/14085 | 5/1995 |
| WO | WO 95/15381 | 6/1995 |

OTHER PUBLICATIONS

U.S. application No. 09/912,293, Rosen et al.
Dorland's Medical Dictionary, p. 232 (1995).
Okubo et al., Large Scale cDNA sequencing for analysis of quantitative and qualitative aspects of gene expression, *Nature Genetics*, 2:173–179 (1992).
Application Serial No. 08/154,792.
Application Serial No. 08/163,449.
Application Serial No. 08/168,877.
Application Serial No. 08/209,521.
Application Serial No. 08/259,310.
Auffray et al, Berkank Accession No. 236291 (Aug. 15, 1994).
Okubo et al, Genbank Accession No. Humosis A10)(Dec. 1, 1992).
Chauhan et al. (1996) Gastroenterol (Suppl.) 110(4):A502.
Goldberg et al. (1993) Clin Chem 39(11B):2360–2374.
Green et al. (1991) Genomics 11:548–564.
Horii et al. (1994) Biochem & Biophys. Res. Comm. 204(3):1257–1264.
Jacoby et al. (1995) Gastroenterology 109(1):73–82.
Nicolaides et al. (1994) Nature 371:75–80.
Nystrom–Lahti et al. (1994) Am J. Human Genes 55:659–665.
Papadopoulos (1994) Science 263:1625–1629.
Prolla et al. (1994) Science 265:1091–1093.
Radman et al. (1993) Biotech. & Genet. Eng. Rev. 11:357–366.
U.S. application No. 08/352.902, Liskay et al., filed Dec. 9, 1994.
U.S. application No. 08/209,521, Liskay et al., filed Mar. 8, 1994.
U.S. application No. 08/168,877, Liskay et al., filed Dec. 17, 1993.
Genexpress, GenBank Database, Submission No. HSB09H062, Jul. 30, 1993.*
Kramer et al., J. of Bacteriology (Oct., 1989), vol. 171(10): pp. 5339–5346.*
Leach, F.S. et al., Mutations of a MutS Homolog in Hereditary Non polyposis Colorectal Cancer, Cell, 75:1215–1225 (1993).
Bronner, C.E., et al., Mutation in the DNA Mismatch repair Gene Homologue LmLH1 is Associated with Hereditary Non–Polyposis Colon Cancer, Nature 368:258–261 (1994).
Fischel, R. et al. The Human Mutator Gene Homolog MSH2 and its Association with Hereditary Nonpolyposis Colon Cancer, Cell, 75:1027–1038 (1993).
Lindblom, A., et al., Genetic Mapping of a Second Locus Predisposing to Hereditary Non–Polyposis Colon Cancer, Nature Genetics, 5:279–287 (1993).

* cited by examiner

*Primary Examiner*—Terry McKelvey
(74) *Attorney, Agent, or Firm*—Human Genome Sciences, Inc.

(57) ABSTRACT

The present invention discloses three human DNA repair proteins and DNA (RNA) encoding such proteins. The DNA repair proteins may be produced by recombinant DNA techniques. One of the human DNA repair proteins, hmlh1, has been mapped on chromosome 3. The polynucleotide sequences of DNA repair proteins may be used for diagnosis of a hereditary susceptibility to cancer.

26 Claims, 8 Drawing Sheets

Polynucleotide and deduced amino acid sequence of hMLH1

```
-40                 -20                  1
.         .         .         .         .         .
GTTGAACATCTAGACGTTTCCTTGGCTCTTCTGGCGCCAAAATGTCGTTCGTGGCAGGGG
+---------+---------+---------+---------+---------+---------
CAACTTGTAGATCTGCAAAGGAACCGAGAAGACCGCGGTTTTACAGCAAGCACCGTCCCC
                                          M  S  F  V  A  G  V 20                  40                   60
.         .         .         .         .         .
TTATTCGGCGGCTGGACGAGACAGTGGTGAACCGCATCGCGGCGGGGGAAGTTATCCAGC
+---------+---------+---------+---------+---------+---------
AATAAGCCGCCGACCTGCTCTGTCACCACTTGGCGTAGCGCCGCCCCCTTCAATAGGTCG
   I  R  R  L  D  E  T  V  V  N  R  I  A  A  G  E  V  I  Q  R 80                  100                  120
.         .         .         .         .         .
GGCCAGCTAATGCTATCAAAGAGATGATTGAGAACTGTTTAGATGCAAAATCCACAAGTA
+---------+---------+---------+---------+---------+---------
CCGGTCGATTACGATAGTTTCTCTACTAACTCTTGACAAATCTACGTTTTAGGTGTTCAT
   P  A  N  A  I  K  E  M  I  E  N  C  L  D  A  K  S  T  S  I 140                 160                  180
.         .         .         .         .         .
TTCAAGTGATTGTTAAAGAGGGAGGCCTGAAGTTGATTCAGATCCAAGACAATGGCACCG
+---------+---------+---------+---------+---------+---------
AAGTTCACTAACAATTTCTCCCTCCGGACTTCAACTAAGTCTAGGTTCTGTTACCGTGGC
   Q  V  I  V  K  E  G  G  L  K  L  I  Q  I  Q  D  N  G  T  G 200                 220                  240
.         .         .         .         .         .
GGATCAGGAAAGAAGATCTGGATATTGTATGTGAAAGGTTCACTACTAGTAAACTGCAGT
+---------+---------+---------+---------+---------+---------
CCTAGTCCTTTCTTCTAGACCTATAACATACACTTTCCAAGTGATGATCATTTGACGTCA
   I  R  K  E  D  L  D  I  V  C  E  R  F  T  T  S  K  L  Q  S 260                 280                  300
.         .         .         .         .         .
CCTTTGAGGATTTAGCCAGTATTTCTACCTATGGCTTTCGAGGTGAGGCTTTGGCCAGCA
+---------+---------+---------+---------+---------+---------
GGAAACTCCTAAATCGGTCATAAAGATGGATACCGAAAGCTCCACTCCGAAACCGGTCGT
   F  E  D  L  A  S  I  S  T  Y  G  F  R  G  E  A  L  A  S  I 320                 340                  360
.         .         .         .         .         .
TAAGCCATGTGGCTCATGTTACTATTACAACGAAAACAGCTGATGGAAAGTGTGCATACA
+---------+---------+---------+---------+---------+---------
ATTCGGTACACCGAGTACAATGATAATGTTGCTTTTGTCGACTACCTTTCACACGTATGT
   S  H  V  A  H  V  T  I  T  T  K  T  A  D  G  K  C  A  Y  R
```

FIG. 1A

```
            380              400              420
             .                .                .
             .                .                .
GAGCAAGTTACTCAGATGGAAAACTGAAAGCCCCTCCTAAACCATGTGCTGGCAATCAAG
+---------+---------+---------+---------+---------+---------
CTCGTTCAATGAGTCTACCTTTTGACTTTCGGGGAGGATTTGGTACACGACCGTTAGTTC
   A  S  Y  S  D  G  K  L  K  A  P  P  K  ?  C  A  G  N  Q  G
   440              460              480
    .                .                .
    .                .                .
GGACCCAGATCACGGTGGAGGACCTTTTTTACAACATAGCCACGAGGAGAAAAGCTTTAA
+---------+---------+---------+---------+---------+---------
CCTGGGTCTAGTGCCACCTCCTGGAAAAAATGTTGTATCGGTGCTCCTCTTTTCGAAATT
    T  Q  I  T  V  E  D  L  F  Y  N  I  A  T  R  R  K  A  L  K
   500              520              540
    .                .                .
    .                .                .
AAAATCCAAGTGAAGAATATGGGAAAATTTTGGAAGTTGTTGGCAGGTATTCAGTACACA
+---------+---------+---------+---------+---------+---------
TTTTAGGTTCACTTCTTATACCCTTTTAAAACCTTCAACAACCGTCCATAAGTCATGTGT
    N  P  S  E  E  Y  G  K  I  L  E  V  V  G  R  Y  S  V  H  N
   560              580              600
    .                .                .
    .                .                .
ATGCAGGCATTAGTTTCTCAGTTAAAAAACAAGGAGAGACAGTAGCTGATGTTAGGACAC
+---------+---------+---------+---------+---------+---------
TACGTCCGTAATCAAAGAGTCAATTTTTTGTTCCTCTCTGTCATCGACTACAATCCTGTG
    A  G  I  S  F  S  V  K  K  Q  G  E  T  V  A  D  V  R  T  L
   620              640              660
    .                .                .
    .                .                .
TACCCAATGCCTCAACCGTGGACAATATTCGCTCCGTCTTTGGGAATGCTGTTAGTCGAG
+---------+---------+---------+---------+---------+---------
ATGGGTTACGGAGTTGGCACCTGTTATAAGCGAGGCAGAAACCCTTACGACAATCAGCTC
    P  N  A  S  T  V  D  N  I  R  S  V  F  G  N  A  V  S  R  E
   680              700              720
    .                .                .
    .                .                .
AACTGATAGAAATTGGATGTGAGGATAAAACCCTAGCCTTCAAAATGAATGGTTACATAT
+---------+---------+---------+---------+---------+---------
TTGACTATCTTTAACCTACACTCCTATTTTGGGATCGGAAGTTTTACTTACCAATGTATA
    L  I  E  I  G  C  E  D  K  T  L  A  F  K  M  N  G  Y  I  S
   740              760              780
    .                .                .
    .                .                .
CCAATGCAAACTACTCAGTGAAGAAGTGCATCTTCTTACTCTTCATCAACCATCGTCTGG
+---------+---------+---------+-------------------+---------
GGTTACGTTTGATGAGTCACTTCTTCACGTAGAAGAATGAGAAGTAGTTGGTAGCAGACC
    N  A  N  Y  S  V  K  K  C  I  F  L  L  F  I  N  H  R  L  V
```

FIG. 1B

```
        800                820                840
          .                  .                  .
          .                  .                  .
TAGAATCAACTTCCTTGAGAAAAGCCATAGAAACAGTGTATGCAGCCTATTTGCCCAAAA
+---------+---------+---------+---------+---------+---------
ATCTTAGTTGAAGGAACTCTTTTCGGTATCTTTGTCACATACGTCGGATAAACGGGTTTT
   E  S  T  S  L  R  K  A  I  E  T  V  Y  A  A  Y  L  P  K  N
        860                880                900
          .                  .                  .
          .                  .                  .
ACACACACCCATTCCTGTACCTCAGTTTAGAAATCAGTCCCCAGAATGTGGATGTTAATG
+---------+---------+---------+---------+---------+---------
TGTGTGTGGGTAAGGACATGGAGTCAAATCTTTAGTCAGGGGTCTTACACCTACAATTAC
   T  H  P  F  L  Y  L  S  L  E  I  S  P  Q  N  V  D  V  N  V
        920                940                960
          .                  .                  .
          .                  .                  .
TGCACCCCACAAAGCATGAAGTTCACTTCCTGCACGAGGAGAGCATCCTGGAGCGGGTGC
+---------+---------+---------+---------+---------+---------
ACGTGGGGTGTTTCGTACTTCAAGTGAAGGACGTGCTCCTCTCGTAGGACCTCGCCCACG
   H  P  T  K  H  E  V  H  F  L  H  E  E  S  I  L  E  R  V  Q
        980               1000               1020
          .                  .                  .
          .                  .                  .
AGCAGCACATCGAGAGCAAGCTCCTGGGCTCCAATTCCTCCAGGATGTACTTCACCCAGA
+---------+---------+---------+---------+---------+---------
TCGTCGTGTAGCTCTCGTTCGAGGACCCGAGGTTAAGGAGGTCCTACATGAAGTGGGTCT
   Q  H  I  E  S  K  L  L  G  S  N  S  S  R  M  Y  F  T  Q  T
       1040               1060               1080
          .                  .                  .
          .                  .                  .
CTTTGCTACCAGGACTTGCTGCCCCTCTGGGGAGATGGTTAAATCCACAACAAGTCTGA
+---------+---------+---------+---------+---------+---------
GAAACGATGGTCCTGAACGACGGGGGAGACCCCTCTACCAATTTAGGTGTTGTTCAGACT
   L  L  P  G  L  A  A  P  S  G  E  M  V  K  S  T  T  S  L  T
       1100               1120               1140
          .                  .                  .
          .                  .                  .
CCTCGTCTTCTACTTCTGGAAGTAGTGATAAGGTCTATGCCCACCAGATGGTTCGTACAG
+---------+---------+---------+---------+---------+---------
GGAGCAGAAGATGAAGACCTTCATCACTATTCCAGATACGGGTGGTCTACCAAGCATGTC
   S  S  S  T  S  G  S  S  D  K  V  Y  A  H  Q  M  V  R  T  D
       1160               1180               1200
          .                  .                  .
          .                  .                  .
ATTCCCGGGAACAGAAGCTTGATGCATTTCTGCAGCCTCTGAGCAAACCCCTGTCCAGTC
+---------+---------+---------+---------+---------+---------
TAAGGGCCCTTGTCTTCGAACTACGTAAAGACGTCGGAGACTCGTTTGGGGACAGGTCAG
   S  R  E  Q  K  L  D  A  F  L  Q  P  L  S  K  P  L  S  S  Q
```

FIG. 1C

```
1220                1240                1260
  .                   .                   .
AGCCCCAGGCCATTGTCACAGAGGATAAGACAGATATTTCTAGTGGCAGGGCTAGGCAGC
+---------+---------+---------+---------+---------+---------
TCGGGGTCCGGTAACAGTGTCTCCTATTCTGTCTATAAAGATCACCGTCCCGATCCGTCG
   P  Q  A  I  V  T  E  D  K  T  D  I  S  S  G  R  A  R  Q  Q
1280                1300                1320
  .                   .                   .
AAGATGAGGAGATGCTTGAACTCCCAGCCCCTGCTGAAGTGGCTGCCAAAAATCAGAGCT
+---------+---------+---------+---------+---------+---------
TTCTACTCCTCTACGAACTTGAGGGTCGGGGACGACTTCACCGACGGTTTTTAGTCTCGA
    D  E  E  M  L  E  L  P  A  P  A  E  V  A  A  K  N  Q  S  L
1340                1360                1380
  .                   .                   .
TGGAGGGGGATACAACAAAGGGGACTTCAGAAATGTCAGAGAAGAGAGGACCTACTTCCA
+---------+---------+---------+---------+---------+---------
ACCTCCCCCTATGTTGTTTCCCCTGAAGTCTTTACAGTCTCTTCTCTCCTGGATGAAGGT
    E  G  D  T  T  K  G  T  S  E  M  S  E  K  R  G  P  T  S  S
1400                1420                1440
  .                   .                   .
GCAACCCCAGAAAGAGACATCGGGAAGATTCTGATGTGGAAATGGTGGAAGATGATTCCC
+---------+---------+---------+---------+---------+---------
CGTTGGGGTCTTTCTCTGTAGCCCTTCTAAGACTACACCTTTACCACCTTCTACTAAGGG
    N  P  R  K  R  H  R  E  D  S  D  V  E  M  V  E  D  D  S  R
1460                1480                1500
  .                   .                   .
GAAAGGAAATGACTGCAGCTTGTACCCCCCGGAGAAGGATCATTAACCTCACTAGTGTTT
+---------+---------+---------+---------+---------+---------
CTTTCCTTTACTGACGTCGAACATGGGGGGCCTCTTCCTAGTAATTGGAGTGATCACAAA
    K  E  M  T  A  A  C  T  P  R  R  R  I  I  N  L  T  S  V  L
1520                1540                1560
  .                   .                   .
TGAGTCTCCAGGAAGAAATTAATGAGCAGGGACATGAGGTTCTCCGGGAGATGTTGCATA
+---------+---------+---------+---------+---------+---------
ACTCAGAGGTCCTTCTTTAATTACTCGTCCCTGTACTCCAAGAGGCCCTCTACAACGTAT
    S  L  Q  E  E  I  N  E  Q  G  H  E  V  L  R  E  M  L  H  N
1580                1600                1620
  .                   .                   .
ACCACTCCTTCGTGGGCTGTGTGAATCCTCAGTGGGCCTTGGCACAGCATCAAACCAAGT
+---------+---------+---------+---------+---------+---------
TGGTGAGGAAGCACCCGACACACTTAGGAGTCACCCGGAACCGTGTCGTAGTTTGGTTCA
    H  S  F  V  G  C  V  N  P  Q  W  A  L  A  Q  H  Q  T  K  L
```

FIG. 1D

```
                 1640                1660                1680
                  .                   .                   .
       .         .         .         .         .         .
TATACCTTCTCAACACCACCAAGCTTAGTGAAGAACTGTTCTACCAGATACTCATTTATG
+---------+---------+---------+---------+---------+---------
ATATGGAAGAGTTGTGGTGGTTCGAATCACTTCTTGACAAGATGGTCTATGAGTAAATAC
   Y  L  L  N  T  T  K  L  S  E  E  L  F  Y  Q  I  L  I  Y  D
  1700                1720                1740
   .                   .                   .
       .         .         .         .         .         .
ATTTTGCCAATTTTGGTGTTCTCAGGTTATCGGAGCCAGCACCGCTCTTTGACCTTGCCA
+---------+---------+---------+---------+---------+---------
TAAAACGGTTAAAACCACAAGAGTCCAATAGCCTCGGTCGTGGCGAGAAACTGGAACGGT
   F  A  N  F  G  V  L  R  L  S  E  P  A  P  L  F  D  L  A  M
  1760                1730                1800
   .                   .                   .
       .         .         .         .         .         .
TGCTTGCCTTAGATAGTCCAGAGAGTGGCTGGACAGAGGAAGATGGTCCCAAAGAAGGAC
+---------+---------+---------+---------+---------+---------
ACGAACGGAATCTATCAGGTCTCTCACCGACCTGTCTCCTTCTACCAGGGTTTCTTCCTG
   L  A  L  D  S  P  E  S  G  W  T  E  E  D  G  P  K  E  G  L
  1820                1840                1860
   .                   .                   .
       .         .         .         .         .         .
TTGCTGAATACATTGTTGAGTTTCTGAAGAAGAAGGCTGAGATGCTTGCAGACTATTTCT
+---------+---------+---------+---------+---------+---------
AACGACTTATGTAACAACTCAAAGACTTCTTCTTCCGACTCTACGAACGTCTGATAAAGA
   A  E  Y  I  V  E  F  L  K  K  K  A  E  M  L  A  D  Y  F  S
  1880                1900                1920
   .                   .                   .
       .         .         .         .         .         .
CTTTGGAAATTGATGAGGAAGGGAACCTGATTGGATTACCCCTTCTGATTGACAACTATG
+---------+---------+---------+---------+---------+---------
GAAACCTTTAACTACTCCTTCCCTTGGACTAACCTAATGGGGAAGACTAACTGTTGATAC
   L  E  I  D  E  E  G  N  L  I  G  L  P  L  L  I  D  N  Y  V
  1940                1960                1980
   .                   .                   .
       .         .         .         .         .         .
TGCCCCCTTTGGAGGGACTGCCTATCTTCATTCTTCGACTAGCCACTGAGGTGAATTGGG
---------+---------+---------+---------+---------+---------+
ACGGGGGAAACCTCCCTGACGGATAGAAGTAAGAAGCTGATCGGTGACTCCACTTAACCC
   P  P  L  E  G  L  P  I  F  I  L  R  L  A  T  E  V  N  W  D
  2000                2020                2040
   .                   .                   .
       .         .         .         .         .         .
ACGAAGAAAAGGAATGTTTTGAAAGCCTCAGTAAAGAATGCGCTATGTTCTATTCCATCC
+---------+---------+---------+---------+---------+---------
TGCTTCTTTTCCTTACAAAACTTTCGGAGTCATTTCTTACGCGATACAAGATAAGGTAGG
   E  E  K  E  C  F  E  S  L  S  K  E  C  A  M  F  Y  S  I  R
```

FIG. 1E

```
                  2060              2080              2100
                    .                 .                 .
       GGAAGCAGTACATATCTGAGGAGTCGACCCTCTCAGGCCAGCAGAGTGAAGTGCCTGGCT
       +---------+---------+---------+---------+---------+---------
       CCTTCGTCATGTATAGACTCCTCAGCTGGGAGAGTCCGGTCGTCTCACTTCACGGACCGA
          K  Q  Y  I  S  E  E  S  T  L  S  G  Q  Q  S  E  V  P  G  S
       2120              2140              2160
         .                 .                 .
       CCATTCCAAACTCCTGGAAGTGGACTGTGGAACACATTGTCTATAAAGCCTTGCGCTCAC
       +---------+---------+---------+---------+---------+---------
       GGTAAGGTTTGAGGACCTTCACCTGACACCTTGTGTAACAGATATTTCGGAACGCGAGTG
           I  P  N  S  W  K  W  T  V  E  H  I  V  Y  K  A  L  R  S  H
       2180              2200              2220
         .                 .                 .
       ACATTCTGCCTCCTAAACATTTCACAGAAGATGGAAATATCCTGCAGCTTGCTAACCTGC
       +---------+---------+---------+---------+---------+---------
       TGTAAGACGGAGGATTTGTAAAGTGTCTTCTACCTTTATAGGACGTCGAACGATTGGACG
           I  L  P  P  K  H  F  T  E  D  G  N  I  L  Q  L  A  N  L  P
       2240              2260              2280
         .                 .                 .
       CTGATCTATACAAAGTCTTTGAGAGGTGTTAAATATGGTTATTTATGCACTGTGGGATGT
       +---------+---------+---------+---------+---------+---------
       GACTAGATATGTTTCAGAAACTCTCCACAATTTATACCAATAAATACGTGACACCCTACA
           D  L  Y  K  V  F  E  R  C  *
       2300              2320              2340
         .                 .                 .
       GTTCTTCTTTCTCTGTATTCCGATACAAAGTGTTGTATCAAAGTGTGATATACAAAGTGT
       +---------+---------+---------+---------+---------+---------
       CAAGAAGAAAGAGACATAAGGCTATGTTTCACAACATAGTTTCACACTATATGTTTCACA
       2360              2380              2400
         .                 .                 .
       ACCAACATAAGTGTTGGTAGCACTTAAGACTTATACTTGCCTTCTGATAGTATTCCTTTA
       +---------+---------+---------+---------+---------+---------
       TGGTTGTATTCACAACCATCGTGAATTCTGAATATGAACGGAAGACTATCATAAGGAAAT
       2420              2440              2460
         .                 .                 .
       TACACAGTGGATTGATTATAAATAAATAGATGTGTCTTAACATAAAAAAAAAAAAAAAAA
       +--------------------+---------+---------+---------+---------
       ATGTGTCACCTAACTAATATTTATTTATCTACACAGAATTGTATTTTTTTTTTTTTTTTT

2480
         .
       AAAAA
       +----
       TTTTT
```

FIG. 1F

Est sequence of hMLH2

```
  1 TGGCTGCTTG CGGCTAGTGG ATGGTAATTG CCTGCCTCGC GCTANAGCAA

51 GCTGCTCTGT TAAAAGCGAA AATGAAACAA TTGCCTGCGG CAACAGTTCG

101 ACTCCTTTCA AGTTCTCAGA TCATCACTTC GGTGGTCAGT GTTGTAAAAG

151 AGCTTATTGA AAACTCCTTG GATGCTGGTG CCACAAGCGT AGATGTTAAA

201 CTGGAGAACT ATGGATTTGA TAAAATTGAG GTNCGAGATA ACGGGGAGGG

251 TATCAAGGCT GTTTATGCAC CTGTAATGGC AATGAAGTAC TACACCTCAA

301 AATTAAATTA GTCATGATGA TCTTGAA
```

FIG. 1G

Est sequence of hMLH3

```
  1 CCGAGGCGGA TCGGGTGTTG CATCCATGGA GCGAGCTGAG AGCTCGAGTA

51 CAGAACCTGC TAAGGCCATC AAACCTATTG ATCGGAAGTC AGTCCATCAG

101 ATTTGCTCTG GGCAGGTGGT ACTGAGTCTA AGCACTGCGG TAAAGGAGTT

151 AGTAGAAAAC AGTCTGGATG CTGGTGCCAC TAATATTGAT CTAAAGCTTA

201 AGGACTATGG AGTGGATCTT ATTGAAGTTT CAGACAATGG ATGTGGGGTA

251 GAAGAAGAAA ACTTCGAAGG CTTAACTCTG AAACATCACA CATCTAAGAT

301 TCAAGAGTTT T
```

FIG. 1H

SEQUENCE LISTING

<160> NUMBER OF SEQ ID NOS: 33

<210> SEQ ID NO 1
<211> LENGTH: 2525
<212> TYPE: DNA
<213> ORGANISM: homo sapiens
<220> FEATURE:
<221> NAME/KEY: CDS
<222> LOCATION: (42)..(2312)

-continued

<400> SEQUENCE: 1

```
gttgaacatc tagacgtttc cttggctctt ctggcgccaa a atg tcg ttc gtg gca        56
                                              Met Ser Phe Val Ala
                                               1               5 ggg gtt att cgg cgg ctg gac gag aca gtg gtg aac cgc atc gcg gcg         104
Gly Val Ile Arg Arg Leu Asp Glu Thr Val Val Asn Arg Ile Ala Ala
             10                  15                  20 ggg gaa gtt atc cag cgg cca gct aat gct atc aaa gag atg att gag         152
Gly Glu Val Ile Gln Arg Pro Ala Asn Ala Ile Lys Glu Met Ile Glu
         25                  30                  35 aac tgt tta gat gca aaa tcc aca agt att caa gtg att gtt aaa gag         200
Asn Cys Leu Asp Ala Lys Ser Thr Ser Ile Gln Val Ile Val Lys Glu
     40                  45                  50 gga ggc ctg aag ttg att cag atc caa gac aat ggc acc ggg atc agg         248
Gly Gly Leu Lys Leu Ile Gln Ile Gln Asp Asn Gly Thr Gly Ile Arg
 55                  60                  65 aaa gaa gat ctg gat att gta tgt gaa agg ttc act act agt aaa ctg         296
Lys Glu Asp Leu Asp Ile Val Cys Glu Arg Phe Thr Thr Ser Lys Leu
 70                  75                  80                  85 cag tcc ttt gag gat tta gcc agt att tct acc tat ggc ttt cga ggt         344
Gln Ser Phe Glu Asp Leu Ala Ser Ile Ser Thr Tyr Gly Phe Arg Gly
             90                  95                 100 gag gct ttg gcc agc ata agc cat gtg gct cat gtt act att aca acg         392
Glu Ala Leu Ala Ser Ile Ser His Val Ala His Val Thr Ile Thr Thr
         105                 110                 115 aaa aca gct gat gga aag tgt gca tac aga gca agt tac tca gat gga         440
Lys Thr Ala Asp Gly Lys Cys Ala Tyr Arg Ala Ser Tyr Ser Asp Gly
     120                 125                 130 aaa ctg aaa gcc cct cct aaa cca tgt gct ggc aat caa ggg acc cag         488
Lys Leu Lys Ala Pro Pro Lys Pro Cys Ala Gly Asn Gln Gly Thr Gln
 135                 140                 145 atc acg gtg gag gac ctt ttt tac aac ata gcc acg agg aga aaa gct         536
Ile Thr Val Glu Asp Leu Phe Tyr Asn Ile Ala Thr Arg Arg Lys Ala
150                 155                 160                 165 tta aaa aat cca agt gaa gaa tat ggg aaa att ttg gaa gtt gtt ggc         584
Leu Lys Asn Pro Ser Glu Glu Tyr Gly Lys Ile Leu Glu Val Val Gly
             170                 175                 180 agg tat tca gta cac aat gca ggc att agt ttc tca gtt aaa aaa caa         632
Arg Tyr Ser Val His Asn Ala Gly Ile Ser Phe Ser Val Lys Lys Gln
         185                 190                 195 gga gag aca gta gct gat gtt agg aca cta ccc aat gcc tca acc gtg         680
Gly Glu Thr Val Ala Asp Val Arg Thr Leu Pro Asn Ala Ser Thr Val
     200                 205                 210 gac aat att cgc tcc gtc ttt ggg aat gct gtt agt cga gaa ctg ata         728
Asp Asn Ile Arg Ser Val Phe Gly Asn Ala Val Ser Arg Glu Leu Ile
215                 220                 225 gaa att gga tgt gag gat aaa acc cta gcc ttc aaa atg aat ggt tac         776
Glu Ile Gly Cys Glu Asp Lys Thr Leu Ala Phe Lys Met Asn Gly Tyr
230                 235                 240                 245 ata tcc aat gca aac tac tca gtg aag aag tgc atc ttc tta ctc ttc         824
Ile Ser Asn Ala Asn Tyr Ser Val Lys Lys Cys Ile Phe Leu Leu Phe
             250                 255                 260 atc aac cat cgt ctg gta gaa tca act tcc ttg aga aaa gcc ata gaa         872
Ile Asn His Arg Leu Val Glu Ser Thr Ser Leu Arg Lys Ala Ile Glu
         265                 270                 275 aca gtg tat gca gcc tat ttg ccc aaa aac aca cac cca ttc ctg tac         920
Thr Val Tyr Ala Ala Tyr Leu Pro Lys Asn Thr His Pro Phe Leu Tyr
     280                 285                 290
```

```
ctc agt tta gaa atc agt ccc cag aat gtg gat gtt aat gtg cac ccc      968
Leu Ser Leu Glu Ile Ser Pro Gln Asn Val Asp Val Asn Val His Pro
    295                 300                 305 aca aag cat gaa gtt cac ttc ctg cac gag gag agc atc ctg gag cgg     1016
Thr Lys His Glu Val His Phe Leu His Glu Glu Ser Ile Leu Glu Arg
310                 315                 320                 325 gtg cag cag cac atc gag agc aag ctc ctg ggc tcc aat tcc tcc agg     1064
Val Gln Gln His Ile Glu Ser Lys Leu Leu Gly Ser Asn Ser Ser Arg
                330                 335                 340 atg tac ttc acc cag act ttg cta cca gga ctt gct gcc ccc tct ggg     1112
Met Tyr Phe Thr Gln Thr Leu Leu Pro Gly Leu Ala Ala Pro Ser Gly
            345                 350                 355 gag atg gtt aaa tcc aca aca agt ctg acc tcg tct tct act tct gga     1160
Glu Met Val Lys Ser Thr Thr Ser Leu Thr Ser Ser Ser Thr Ser Gly
        360                 365                 370 agt agt gat aag gtc tat gcc cac cag atg gtt cgt aca gat tcc cgg     1208
Ser Ser Asp Lys Val Tyr Ala His Gln Met Val Arg Thr Asp Ser Arg
    375                 380                 385 gaa cag aag ctt gat gca ttt ctg cag cct ctg agc aaa ccc ctg tcc     1256
Glu Gln Lys Leu Asp Ala Phe Leu Gln Pro Leu Ser Lys Pro Leu Ser
390                 395                 400                 405 agt cag ccc cag gcc att gtc aca gag gat aag aca gat att tct agt     1304
Ser Gln Pro Gln Ala Ile Val Thr Glu Asp Lys Thr Asp Ile Ser Ser
                410                 415                 420 ggc agg gct agg cag caa gat gag gag atg ctt gaa ctc cca gcc cct     1352
Gly Arg Ala Arg Gln Gln Asp Glu Glu Met Leu Glu Leu Pro Ala Pro
            425                 430                 435 gct gaa gtg gct gcc aaa aat cag agc ttg gag ggg gat aca aca aag     1400
Ala Glu Val Ala Ala Lys Asn Gln Ser Leu Glu Gly Asp Thr Thr Lys
        440                 445                 450 ggg act tca gaa atg tca gag aag aga gga cct act tcc agc aac ccc     1448
Gly Thr Ser Glu Met Ser Glu Lys Arg Gly Pro Thr Ser Ser Asn Pro
    455                 460                 465 aga aag aga cat cgg gaa gat tct gat gtg gaa atg gtg gaa gat gat     1496
Arg Lys Arg His Arg Glu Asp Ser Asp Val Glu Met Val Glu Asp Asp
470                 475                 480                 485 tcc cga aag gaa atg act gca gct tgt acc ccc cgg aga agg atc att     1544
Ser Arg Lys Glu Met Thr Ala Ala Cys Thr Pro Arg Arg Arg Ile Ile
                490                 495                 500 aac ctc act agt gtt ttg agt ctc cag gaa gaa att aat gag cag gga     1592
Asn Leu Thr Ser Val Leu Ser Leu Gln Glu Glu Ile Asn Glu Gln Gly
            505                 510                 515 cat gag gtt ctc cgg gag atg ttg cat aac cac tcc ttc gtg ggc tgt     1640
His Glu Val Leu Arg Glu Met Leu His Asn His Ser Phe Val Gly Cys
        520                 525                 530 gtg aat cct cag tgg gcc ttg gca cag cat caa acc aag tta tac ctt     1688
Val Asn Pro Gln Trp Ala Leu Ala Gln His Gln Thr Lys Leu Tyr Leu
    535                 540                 545 ctc aac acc acc aag ctt agt gaa gaa ctg ttc tac cag ata ctc att     1736
Leu Asn Thr Thr Lys Leu Ser Glu Glu Leu Phe Tyr Gln Ile Leu Ile
550                 555                 560                 565 tat gat ttt gcc aat ttt ggt gtt ctc agg tta tcg gag cca gca ccg     1784
Tyr Asp Phe Ala Asn Phe Gly Val Leu Arg Leu Ser Glu Pro Ala Pro
                570                 575                 580 ctc ttt gac ctt gcc atg ctt gcc tta gat agt cca gag agt ggc tgg     1832
Leu Phe Asp Leu Ala Met Leu Ala Leu Asp Ser Pro Glu Ser Gly Trp
            585                 590                 595 aca gag gaa gat ggt ccc aaa gaa gga ctt gct gaa tac att gtt gag     1880
Thr Glu Glu Asp Gly Pro Lys Glu Gly Leu Ala Glu Tyr Ile Val Glu
        600                 605                 610
```

-continued

| | | |
|---|---|---|
| ttt ctg aag aag aag gct gag atg ctt gca gac tat ttc tct ttg gaa<br>Phe Leu Lys Lys Lys Ala Glu Met Leu Ala Asp Tyr Phe Ser Leu Glu<br>     615                    620                    625 | 1928 |
| att gat gag gaa ggg aac ctg att gga tta ccc ctt ctg att gac aac<br>Ile Asp Glu Glu Gly Asn Leu Ile Gly Leu Pro Leu Leu Ile Asp Asn<br>630                    635                    640                    645 | 1976 |
| tat gtg ccc cct ttg gag gga ctg cct atc ttc att ctt cga cta gcc<br>Tyr Val Pro Pro Leu Glu Gly Leu Pro Ile Phe Ile Leu Arg Leu Ala<br>               650                    655                    660 | 2024 |
| act gag gtg aat tgg gac gaa gaa aag gaa tgt ttt gaa agc ctc agt<br>Thr Glu Val Asn Trp Asp Glu Glu Lys Glu Cys Phe Glu Ser Leu Ser<br>                   665                    670                    675 | 2072 |
| aaa gaa tgc gct atg ttc tat tcc atc cgg aag cag tac ata tct gag<br>Lys Glu Cys Ala Met Phe Tyr Ser Ile Arg Lys Gln Tyr Ile Ser Glu<br>680                    685                    690 | 2120 |
| gag tcg acc ctc tca ggc cag cag agt gaa gtg cct ggc tcc att cca<br>Glu Ser Thr Leu Ser Gly Gln Gln Ser Glu Val Pro Gly Ser Ile Pro<br>     695                    700                    705 | 2168 |
| aac tcc tgg aag tgg act gtg gaa cac att gtc tat aaa gcc ttg cgc<br>Asn Ser Trp Lys Trp Thr Val Glu His Ile Val Tyr Lys Ala Leu Arg<br>710                    715                    720                    725 | 2216 |
| tca cac att ctg cct cct aaa cat ttc aca gaa gat gga aat atc ctg<br>Ser His Ile Leu Pro Pro Lys His Phe Thr Glu Asp Gly Asn Ile Leu<br>               730                    735                    740 | 2264 |
| cag ctt gct aac ctg cct gat cta tac aaa gtc ttt gag agg tgt taa<br>Gln Leu Ala Asn Leu Pro Asp Leu Tyr Lys Val Phe Glu Arg Cys<br>                   745                    750                    755 | 2312 |
| atatggttat ttatgcactg tgggatgtgt tcttctttct ctgtattccg atacaaagtg | 2372 |
| ttgtatcaaa gtgtgatata caaagtgtac caacataagt gttggtagca cttaagactt | 2432 |
| atacttgcct tctgatagta ttcctttata cacagtggat tgattataaa taaatagatg | 2492 |
| tgtcttaaca taaaaaaaaa aaaaaaaaaa aaa | 2525 |

<210> SEQ ID NO 2
<211> LENGTH: 756
<212> TYPE: PRT
<213> ORGANISM: homo sapiens

<400> SEQUENCE: 2

Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
        115                 120                 125

Ser Tyr Ser Asp Gly Lys Leu Lys Ala Pro Pro Lys Pro Cys Ala Gly
    130                 135                 140

-continued

```
Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
            165                 170                 175

Leu Glu Val Val Gly Arg Tyr Ser Val His Asn Ala Gly Ile Ser Phe
                180                 185                 190

Ser Val Lys Lys Gln Gly Glu Thr Val Ala Asp Val Arg Thr Leu Pro
        195                 200                 205

Asn Ala Ser Thr Val Asp Asn Ile Arg Ser Val Phe Gly Asn Ala Val
        210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
                260                 265                 270

Arg Lys Ala Ile Glu Thr Val Tyr Ala Ala Tyr Leu Pro Lys Asn Thr
        275                 280                 285

His Pro Phe Leu Tyr Leu Ser Leu Glu Ile Ser Pro Gln Asn Val Asp
    290                 295                 300

Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
            340                 345                 350

Ala Ala Pro Ser Gly Glu Met Val Lys Ser Thr Thr Ser Leu Thr Ser
            355                 360                 365

Ser Ser Thr Ser Gly Ser Ser Asp Lys Val Tyr Ala His Gln Met Val
        370                 375                 380

Arg Thr Asp Ser Arg Glu Gln Lys Leu Asp Ala Phe Leu Gln Pro Leu
385                 390                 395                 400

Ser Lys Pro Leu Ser Ser Gln Pro Gln Ala Ile Val Thr Glu Asp Lys
                405                 410                 415

Thr Asp Ile Ser Ser Gly Arg Ala Arg Gln Gln Asp Glu Glu Met Leu
            420                 425                 430

Glu Leu Pro Ala Pro Ala Glu Val Ala Lys Asn Gln Ser Leu Glu
            435                 440                 445

Gly Asp Thr Thr Lys Gly Thr Ser Glu Met Ser Glu Lys Arg Gly Pro
450                 455                 460

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
                485                 490                 495

Arg Arg Arg Ile Ile Asn Leu Thr Ser Val Leu Ser Leu Gln Glu Glu
            500                 505                 510

Ile Asn Glu Gln Gly His Glu Val Leu Arg Glu Met Leu His Asn His
            515                 520                 525

Ser Phe Val Gly Cys Val Asn Pro Gln Trp Ala Leu Ala Gln His Gln
        530                 535                 540

Thr Lys Leu Tyr Leu Leu Asn Thr Thr Lys Leu Ser Glu Glu Leu Phe
545                 550                 555                 560
```

```
Tyr Gln Ile Leu Ile Tyr Asp Phe Ala Asn Phe Gly Val Leu Arg Leu
            565                 570                 575
Ser Glu Pro Ala Pro Leu Phe Asp Leu Ala Met Leu Ala Leu Asp Ser
            580                 585                 590
Pro Glu Ser Gly Trp Thr Glu Asp Gly Pro Lys Glu Gly Leu Ala
        595                 600                 605
Glu Tyr Ile Val Glu Phe Leu Lys Lys Lys Ala Glu Met Leu Ala Asp
        610                 615                 620
Tyr Phe Ser Leu Glu Ile Asp Glu Gly Asn Leu Ile Gly Leu Pro
625                 630                 635                 640
Leu Leu Ile Asp Asn Tyr Val Pro Pro Leu Glu Gly Leu Pro Ile Phe
                645                 650                 655
Ile Leu Arg Leu Ala Thr Glu Val Asn Trp Asp Glu Glu Lys Glu Cys
            660                 665                 670
Phe Glu Ser Leu Ser Lys Glu Cys Ala Met Phe Tyr Ser Ile Arg Lys
            675                 680                 685
Gln Tyr Ile Ser Glu Glu Ser Thr Leu Ser Gly Gln Gln Ser Glu Val
        690                 695                 700
Pro Gly Ser Ile Pro Asn Ser Trp Lys Trp Thr Val Glu His Ile Val
705                 710                 715                 720
Tyr Lys Ala Leu Arg Ser His Ile Leu Pro Pro Lys His Phe Thr Glu
                725                 730                 735
Asp Gly Asn Ile Leu Gln Leu Ala Asn Leu Pro Asp Leu Tyr Lys Val
            740                 745                 750
Phe Glu Arg Cys
        755

<210> SEQ ID NO 3
<211> LENGTH: 327
<212> TYPE: DNA
<213> ORGANISM: Homo sapiens
<220> FEATURE:
<221> NAME/KEY: misc_feature
<222> LOCATION: (45)
<223> OTHER INFORMATION: n equals a,t,g, or c
<221> NAME/KEY: misc_feature
<222> LOCATION: (233)
<223> OTHER INFORMATION: n equals a,t,g, or c

<400> SEQUENCE: 3
tggctgcttg cggctagtgg atggtaattg cctgcctcgc gctanagcaa gctgctctgt      60
taaaagcgaa aatgaaacaa ttgcctgcgg caacagttcg actcctttca agttctcaga     120
tcatcacttc ggtggtcagt gttgtaaaag agcttattga aaactccttg gatgctggtg     180
ccacaagcgt agatgttaaa ctggagaact atggatttga taaaattgag gtncgagata     240
acggggaggg tatcaaggct gtttatgcac ctgtaatggc aatgaagtac tacacctcaa     300
aattaaatta gtcatgatga tcttgaa                                         327

<210> SEQ ID NO 4
<211> LENGTH: 311
<212> TYPE: DNA
<213> ORGANISM: Homo sapiens

<400> SEQUENCE: 4
ccgaggcgga tcgggtgttg catccatgga gcgagctgag agctcgagta cagaacctgc      60
taaggccatc aaacctattg atcggaagtc agtccatcag atttgctctg ggcaggtggt     120
actgagtcta agcactgcgg taaggagtt agtagaaaac agtctggatg ctggtgccac     180
```

```
taatattgat ctaaagctta aggactatgg agtggatctt attgaagttt cagacaatgg      240
atgtggggta gaagaagaaa acttcgaagg cttaactctg aaacatcaca catctaagat      300
tcaagagttt t                                                           311
```

```
<210> SEQ ID NO 5
<211> LENGTH: 20
<212> TYPE: DNA
<213> ORGANISM: Artificial Sequence
<220> FEATURE:
<223> OTHER INFORMATION: hMLH1 sense primer

<400> SEQUENCE: 5
gttgaacatc tagacgtctc                                                  20

<210> SEQ ID NO 6
<211> LENGTH: 19
<212> TYPE: DNA
<213> ORGANISM: Artificial Sequence
<220> FEATURE:
<223> OTHER INFORMATION: hMLH1 sense primer

<400> SEQUENCE: 6
tcgtggcagg ggttattcg                                                   19

<210> SEQ ID NO 7
<211> LENGTH: 19
<212> TYPE: DNA
<213> ORGANISM: Artificial Sequence
<220> FEATURE:
<223> OTHER INFORMATION: hMLH1 sense primer

<400> SEQUENCE: 7
ctacccaatg cctcaaccg                                                   19

<210> SEQ ID NO 8
<211> LENGTH: 22
<212> TYPE: DNA
<213> ORGANISM: Artificial Sequence
<220> FEATURE:
<223> OTHER INFORMATION: hMLH1 sense primer

<400> SEQUENCE: 8
gagaactgat agaaattgga tg                                               22

<210> SEQ ID NO 9
<211> LENGTH: 18
<212> TYPE: DNA
<213> ORGANISM: Artificial Sequence
<220> FEATURE:
<223> OTHER INFORMATION: hMLH1 sense primer

<400> SEQUENCE: 9
gggacatgag gttctccg                                                    18

<210> SEQ ID NO 10
<211> LENGTH: 19
<212> TYPE: DNA
<213> ORGANISM: Artificial Sequence
<220> FEATURE:
<223> OTHER INFORMATION: hMLH1 sense primer

<400> SEQUENCE: 10
gggctgtgtg aatcctcag                                                   19
```

```
<210> SEQ ID NO 11
<211> LENGTH: 20
<212> TYPE: DNA
<213> ORGANISM: Artificial Sequence
<220> FEATURE:
<223> OTHER INFORMATION: hMLH1 antisense primer

<400> SEQUENCE: 11
cggttcacca ctgtctcgtc                                              20

<210> SEQ ID NO 12
<211> LENGTH: 18
<212> TYPE: DNA
<213> ORGANISM: Artificial Sequence
<220> FEATURE:
<223> OTHER INFORMATION: hMLH1 antisense primer

<400> SEQUENCE: 12
tccaggatgc tctcctcg                                                18

<210> SEQ ID NO 13
<211> LENGTH: 20
<212> TYPE: DNA
<213> ORGANISM: Artificial Sequence
<220> FEATURE:
<223> OTHER INFORMATION: hMLH1 antisense primer

<400> SEQUENCE: 13
caagtcctgg tagcaaagtc                                              20

<210> SEQ ID NO 14
<211> LENGTH: 19
<212> TYPE: DNA
<213> ORGANISM: Artificial Sequence
<220> FEATURE:
<223> OTHER INFORMATION: hMLH1 antisense primer

<400> SEQUENCE: 14
atggcaaggt caaagagcg                                               19

<210> SEQ ID NO 15
<211> LENGTH: 22
<212> TYPE: DNA
<213> ORGANISM: Artificial Sequence
<220> FEATURE:
<223> OTHER INFORMATION: hMLH1 antisense primer
<221> NAME/KEY: misc_feature
<222> LOCATION: (22)..(22)
<223> OTHER INFORMATION: n equals a, t, g or c

<400> SEQUENCE: 15
caacaatgta ttcagnaagt cc                                           22

<210> SEQ ID NO 16
<211> LENGTH: 21
<212> TYPE: DNA
<213> ORGANISM: Artificial Sequence
<220> FEATURE:
<223> OTHER INFORMATION: hMLH1 antisense primer

<400> SEQUENCE: 16
ttgatacaac actttgtatc g                                            21

<210> SEQ ID NO 17
<211> LENGTH: 21
<212> TYPE: DNA
```

```
<213> ORGANISM: Artificial Sequence
<220> FEATURE:
<223> OTHER INFORMATION: hMLH1 antisense primer

<400> SEQUENCE: 17
ggaatactat cagaaggcaa g                                              21

<210> SEQ ID NO 18
<211> LENGTH: 21
<212> TYPE: DNA
<213> ORGANISM: Artificial Sequence
<220> FEATURE:
<223> OTHER INFORMATION: hMLH1 sense primer

<400> SEQUENCE: 18
acagagcaag ttactcagat g                                              21

<210> SEQ ID NO 19
<211> LENGTH: 21
<212> TYPE: DNA
<213> ORGANISM: Artificial Sequence
<220> FEATURE:
<223> OTHER INFORMATION: hMLH1 sense primer

<400> SEQUENCE: 19
agtacacaat gcaggcatta g                                              21

<210> SEQ ID NO 20
<211> LENGTH: 21
<212> TYPE: DNA
<213> ORGANISM: Artificial Sequence
<220> FEATURE:
<223> OTHER INFORMATION: hMLH1 sense primer

<400> SEQUENCE: 20
aatgtggatg ttaatgtgca c                                              21

<210> SEQ ID NO 21
<211> LENGTH: 18
<212> TYPE: DNA
<213> ORGANISM: Artificial Sequence
<220> FEATURE:
<223> OTHER INFORMATION: hMLH1 sense primer

<400> SEQUENCE: 21
ctgacctcgt cttcctac                                                  18

<210> SEQ ID NO 22
<211> LENGTH: 19
<212> TYPE: DNA
<213> ORGANISM: Artificial Sequence
<220> FEATURE:
<223> OTHER INFORMATION: hMLH1 sense primer

<400> SEQUENCE: 22
cagcaagatg aggagatgc                                                 19

<210> SEQ ID NO 23
<211> LENGTH: 21
<212> TYPE: DNA
<213> ORGANISM: Artificial Sequence
<220> FEATURE:
<223> OTHER INFORMATION: hMLH1 sense primer

<400> SEQUENCE: 23
ggaaatggtg gaagatgatt c                                              21
```

<210> SEQ ID NO 24
<211> LENGTH: 16
<212> TYPE: DNA
<213> ORGANISM: Artificial Sequence
<220> FEATURE:
<223> OTHER INFORMATION: hMLH1 sense primer

<400> SEQUENCE: 24
cttctcaaca ccaagc                                                     16

<210> SEQ ID NO 25
<211> LENGTH: 21
<212> TYPE: DNA
<213> ORGANISM: Artificial Sequence
<220> FEATURE:
<223> OTHER INFORMATION: hMLH1 sense primer

<400> SEQUENCE: 25
gaaattgatg aggaagggaa c                                               21

<210> SEQ ID NO 26
<211> LENGTH: 22
<212> TYPE: DNA
<213> ORGANISM: Artificial Sequence
<220> FEATURE:
<223> OTHER INFORMATION: hMLH1 sense primer

<400> SEQUENCE: 26
cttctgattg acaactatgt gc                                              22

<210> SEQ ID NO 27
<211> LENGTH: 22
<212> TYPE: DNA
<213> ORGANISM: Artificial Sequence
<220> FEATURE:
<223> OTHER INFORMATION: hMLH1 sense primer

<400> SEQUENCE: 27
cacagaagat ggaaatatcc tg                                              22

<210> SEQ ID NO 28
<211> LENGTH: 20
<212> TYPE: DNA
<213> ORGANISM: Artificial Sequence
<220> FEATURE:
<223> OTHER INFORMATION: hMLH1 sense primer

<400> SEQUENCE: 28
gtgttggtag cacttaagac                                                 20

<210> SEQ ID NO 29
<211> LENGTH: 20
<212> TYPE: DNA
<213> ORGANISM: Artificial Sequence
<220> FEATURE:
<223> OTHER INFORMATION: hMLH1 antisense primer

<400> SEQUENCE: 29
tttcccatat tcttcacttg                                                 20

<210> SEQ ID NO 30
<211> LENGTH: 19
<212> TYPE: DNA
<213> ORGANISM: Artificial Sequence
<220> FEATURE:

```
<223> OTHER INFORMATION: hMLH1 antisense primer

<400> SEQUENCE: 30
gtaacatgag ccacatggc                                              19

<210> SEQ ID NO 31
<211> LENGTH: 19
<212> TYPE: DNA
<213> ORGANISM: Artificial Sequence
<220> FEATURE:
<223> OTHER INFORMATION: hMLH1 antisense primer

<400> SEQUENCE: 31
ccactgtctc gtccagccg                                              19

<210> SEQ ID NO 32
<211> LENGTH: 26
<212> TYPE: DNA
<213> ORGANISM: Artificial Sequence
<220> FEATURE:
<223> OTHER INFORMATION: hMLH1 5' primer with BamHI restriction site

<400> SEQUENCE: 32
cgggatccat gtcgttcgtg gcaggg                                      26

<210> SEQ ID NO 33
<211> LENGTH: 26
<212> TYPE: DNA
<213> ORGANISM: Artificial Sequence
<220> FEATURE:
<223> OTHER INFORMATION: hMLH1 3' primer with XbaI restriction site

<400> SEQUENCE: 33
gctctagatt aacacctctc aaagac                                      26
```

HUMAN DNA MISMATCH REPAIR POLYNUCLEOTIDES

This invention relates to newly identified polynucleotide sequences, polypeptides encoded by such sequences, the use of such polynucleotides and polypeptides, as well as the production of such polynucleotides and polypeptides. More particularly, the polypeptides of the present invention are three human DNA mismatch repair proteins, HMLH1, HMLH2, and HMLH3.

In both procaryotes and eucaryotes, DNA mismatch repair plays a prominent role in the correction of errors made during DNA replication and genetic recombination. The *E. coli* methyl-directed DNA mismatch repair system is the best understood DNA mismatch repair system to date. In *E. coli*, this repair pathway involves the products of the mutator genes mutS, mutL, mutH, and uvrD. Mutants of any one of these genes will reveal a mutator phenotype. MutS is a DNA mismatch-binding protein which initiates this repair process, UvrD is a DNA helicase and MutH is a latent endonuclease that incises at the unmethylated strands of hemimethylated GATC sequence. MutL protein is believed to recognize and bind to the mismatch-DNA-MutS-MutH complex to enhance the endonuclease activity of MutH protein. After the unmethylated DNA strand is cut by the MutH, single-stranded DNA-binding protein, DNA polymerase III, exonuclease I and DNA ligase are required to complete this repair process (Modrich P., *Annu. Rev. Genetics*, 25:229–53 [1991]).

Elements of the *E. coli* MutLHS system appears to be conserved during evolution in procaryotes and eucaryotes. Genetic study analysis suggests that *Saccharomyces cerevisiae* has a mismatch repair system similar to the bacterial MutLHS system. In *S. cerevisiae*, at least two MutL homologs, PMS1 and MLH1, have been reported. Mutation of either one of them leads to a mitotic mutator phenotype (Prolla et al, Mol. Cell. Biol. 14:407–415 [1994]). At least three MutS homologs have been found in *S.cerevisiae*, MSH1, MSH2, and MSH3. Disruption of the msh2 gene affects nuclear mutation rates. Mutants *S. cerevisae* msh2, pms1, and mlh1 have found to exhibit increased rates of expansion and contraction of dinucleotide repeat sequences (Strand et al., Nature, 365:274–276[1993]).

It has been reported by various laboratories that a number of human tumors such as lung cancer, prostate cancer, ovarian cancer, breast cancer, colon cancer and stomach cancer show instability of repeated DNA sequences (Han et al., Cancer, 53:5087–5089[1993]; Thibodeau et al., *Science* 260:816–819[1993]; Risinger et al., Cancer 53:5100–5103 [1993]). This phenomenon suggested that lack of the DNA mismatch repair is probably the cause of these tumors. Little is known about the DNA mismatch repair system in humans until recently, the human homolog of the MutS was cloned and found to be responsible for hereditary nonpolyposis colon cancer (HNPCC).(Fishel et al., *Cell*, 75:1027–1038 [1993] and Leach et al., Cell, 75:1215–1225 [1993]). The HNPCC was first linked to a locus at chromosome 2p16 which causes dinucleotide instability. It was then demonstrated that a DNA mismatch repair protein (MutS) homolog, was located at this locus and C→T transitional mutations at several conserved regions were specifically observed in HNPCC patients.

It has previously been demonstrated that hereditary colon cancer can result from mutations in several loci. Familial adenomatosis polyposis *coli* (APC) linked to a gene on chromosome 5 is responsible for a small minority of hereditary colon cancer. Hereditary colon cancer is also associated with Gardner's syndrome, Turcot's syndrome, Peutz-Jaeghers syndrome and juvenile polyposis *coli*. In addition, hereditary non polyposis colon cancer (HNPCC)may be involved in 5% of all human colon cancer. All of the different types of familial colon cancer have been shown to be transmitted by a dominant autosomal mode of inheritance.

In addition to localization of HNPCC in two families to the short arm of chromosome 2, a second locus has been linked to a predisposition to HNPCC (Lindholm et al. Nature Genetics 1993, 5 279–282). A strong linkage was demonstrated between a polymorphic marker on the short arm of chromosome 3 and the disease locus. It was also suggested that these families show signs of a general defect in the DNA repair process.

This finding suggests that mutations on various DNA mismatch repair proteins probably play crucial role in causing human hereditary diseases and cancers such as lung cancer, prostate cancer, ovarian cancer, breast cancer, colon cancer and stomach cancer.

In accordance with one aspect of the present invention, there is provided three novel polypeptides which are human CDNA mismatch repair proteins, sometimes hereinafter referred to as HMLH1, HMLH2 and HMLH3, as well as analogs and derivatives thereof. The polypeptides of the present invention are of human origin.

In accordance with another aspect of the present invention, there is provided a polynucleotide (DNA) which encodes such polypeptide.

In accordance with still another aspect of the present invention, there is provided a procedure for producing such polypeptide by recombinant techniques.

In accordance with yet a further aspect of the present invention, there is provided a process for using the polypeptide or DNA sequence encoding such polypeptide for diagnostic and therapeutic purposes.

These and other aspects of the present invention should be apparent to those skilled in the art from the teachings herein.

The following drawings are illustrative of embodiments of the invention and are not meant to limit the scope of the invention as encompassed by the claims.

BRIEF DESCRIPTION OF THE DRAWINGS
(SEQ ID NO:1)

FIGS. 1A–1F show the DNA sequence (SEQ ID NO:1) and deduced amino acid sequence (SEQ ID NO:2) for the human DNA repair protein HMLH1. The amino acids are represented by their standard one-letter abbreviations.

FIG. 1G is a partial DNA sequence for the human DNA repair protein HMLH2 (SEQ ID NO:3).

FIG. 1H is a partial DNA sequence for the human DNA repair protein HMLH3 (SEQ ID NO:4).

DESCRIPTION OF THE INVENTION

In accordance with one aspect of the present invention, there is provided a DNA sequence (and corresponding RNA sequence) as set forth in FIGS. 1A–F (SEQ ID NO:1) of the drawings and/or DNA (RNA) sequences encoding the same polypeptide as the sequence of FIGS. 1A–F (SEQ ID NO:1) of the drawings, as well as fragment portions, derivatives, analogs and all allelic variants of such sequences.

In accordance with another aspect of the present invention, there is provided a DNA sequence (and corresponding RNA sequence) which encodes for a human DNA repair protein which DNA sequence contains the partial sequence of FIG. 1G (SEQ ID NO:3).

In accordance with another aspect of the present invention, there is provided a DNA sequence (and corresponding RNA sequence) which encodes for a human DNA repair protein which DNA sequence contains the partial sequence of FIG. 1H (SEQ ID NO:4).

In accordance with another aspect of the present invention, there is provided a polynucleotide which encodes the same polypeptide as the polynucleotide of a cDNA clone deposited as ATCC deposit number 75649, deposited on Jan. 25, 1994 or ATCC Deposit number 75651, deposited on Jan. 25, 1994 or ATCC Deposit number 75650, deposited on Jan. 25, 1994 and/or fragments, analogs, derivatives or allelic variants of such polynucleotide. The address of the ATCC depository referred to herein is ATCC, USA.

ATCC Deposit Number 75649, is a cDNA clone which contains the full length sequence encoding the human DNA repair protein referred to herein as HMLH1; ATCC Deposit Number 75651, is a cDNA clone containing the full length DNA sequence encoding the human DNA repair protein referred to herein as HMLH2; ATCC Deposit Number 75650, is a cDNA clone containing the full length DNA sequence referred to herein as HMLH3.

In the case of DNA, DNA may be single stranded or double stranded, and if single stranded the DNA sequence may be the "sense" strand shown in FIG. 1 (SEQ ID NO:1) or the one complementary thereto.

The polynucleotide (DNA or RNA, preferably DNA) includes at least the portion coding for the polypeptide, which coding portion may be the same as that in the deposited clone or may be different than that in the deposited clone provide that it encodes for the same polypeptide or an allelic variant thereof. The coding portion preferably encodes at least the nature form of the protein of the present invention.

The present invention further relates to polynucleotide sequences which hybridize under stringent conditions to the herein above-described polynucleotide sequences. As herein used, the term "stringent conditions" means hybridization will occur if there is at least 95% and preferably at least 97% identity between the segments. Thus, the present invention includes DNA (RNA) sequences encoding allelic variant forms of the peptide encoded by the DNA of FIG. 1 (SEQ ID NO:1). Thus, the present invention provides isolated DNA (RNA) encoding for a naturally occurring human polypeptide which is a human DNA repair protein as well as allelic variants thereof. The DNA (RNA) is preferably provided in a purified and isolated form.

The present invention further relates to three polypeptides which are three human DNA repair proteins and which, have the structure shown in FIGS. 1A–F (SEQ ID NO:2), 1G (SEQ ID NO:3), and 1H (SEQ ID NO:4), as well as allelic variants thereof, and analogs, fragments and derivatives thereof which have the same function as the naturally occurring polypeptide.

The present invention further relates to a polypeptide encoded by the DNA contained in one of the clones deposited as ATCC number 75689, 75651, or 75650 on Jan. 25, 1994 as well as analogs, fragments, derivatives and allelic variants thereof.

These deposits will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. 112. The sequence of the polynucleotides contained in the deposited materials, as well as the amino acid sequence of the polypeptide encoded thereby, are incorporated herein by reference and are controlling in the event of any conflict with description of sequences herein. A license may be required to make, use or sell the deposited materials, and no such license is hereby granted.

A polypeptide of the present invention is preferably provided in an isolated form, and preferably is purified.

In a preferred embodiment, the human DNA repair proteins are full length mature human proteins or an allelic or glycosylated variant thereof. The polynucleotide may also encode a preprotein which is processed and secreted from mammalian cells as the mature protein.

The polynucleotide sequence of the present invention may encode for the mature form of the polypeptide or may encode for the protein with a leader sequence. For example, the desired DNA sequence may be fused in the same reading frame to a DNA sequence which aids in the expression and secretion of the polypeptide, for example, a leader sequence which acts as a secretory sequence for controlling transportation of the polypeptide from the cell of the host. The protein having a leader sequence is a preprotein and may have the leader sequence cleaved by the host cell to form the mature form of the protein. The polynucleotide of the present invention may also be fused in frame to a marker sequence which allows for purification of the polypeptide of the present invention, for example, a hexa-histidine tag.

Thus, the polypeptide(s) of the present invention may be the mature form of the human DNA repair protein of the present invention; or may be in the form of a preprotein or prepolypeptide wherein the human DNA repair protein includes a leader or signal sequence; or may be in the form of a fusion protein wherein additional amino acids which aid in, for example, purification of the polypeptide are fused to the mature or preprotein at either the 3' or 5' end thereof.

As herein above indicated, the present invention also includes variants of the polypeptide which is encoded by the DNA of the drawings 1 or and variants of the DNA contained in the deposited clones, which retains the DNA repair activity of such a polypeptide. The variant may be a substitutional variant, or an insertion variant or a deletional variant. Such variants can be naturally occurring allelic variants such as for example, those with different glycosylation patterns or substitution at the amino acid level or deletion at the amino acid level.

A polynucleotide encoding a polypeptide of the present invention may be obtained from one or more libraries prepared from one of the following tissues: heart, lung, prostate, spleen, liver, gall bladder, fetal brain, and testis. The polynucleotides of HMLH1, HMLH2 and HMLH3 are from human gall bladder, human T-cell lymphoma and human endometrial tumor cDNA libraries. In addition, six cDNA clones which are identical to the hmlh1 at N-terminal ends were obtained from human cerebellum, 8-week embryo, fetal heart, HSC172 cells and Jurket cell cDNA libraries. A second hmlh3 gene has also been found in human Supt cell cDNA library. All three human DNA repair genes share significant homology to *E. coli* and yeast mutL protein at the amino acid level. The first 200 amino acids of hmlh1 has 44% identity and 64% similarity to *E. Coli* mutL. The partial HMLH2 gene has 37% identity and 65% similarity to yeast pms1 on an amino acid basis. The partial HMLH3 gene has 55% identity and 79% similarity to yeast pms1 gene on an amino acid basis. The HMLH1 contains an open reading frame of 756 amino acids encoding for an 85 kD protein which exhibit homology to bacteria and yeast MutL protein. The coding sequence of HMLH1 has been derived from the cDNA clone obtained from the gall bladder. However, the 5' non-translational region was from the cDNA clone obtained from the fetal heart for the purpose fo extending the non-translational region to design the oligonucleotides.

Host cells are transformed with the expression vectors of this invention and cultured in conventional nutrient media modified as appropriate for including promoters, selecting transformants or expressing the hmlh1 to complement the host mutator phenotype.

"Transformation" means introducing DNA into an organism so that the DNA is replicable, either as an extrachromosomal element or by chromosomal integration. Unless indicated otherwise, the method used herein for transformation of the host cells is the method of Graham, F. and Van der Eb, A., *Virology* 52:456–457 (1973). However, other methods for introducing DNA into cells such as by nuclear injection or by protoplast fusion may also be used. If prokaryotic cells or cells which contain substantial cell wall constructions are used, the preferred method of transfection is calcium treatment using calcium chloride as described by Cohen, F. N. et al., *Proc. Natl. Acad. Sci.* (USA), 69:2110 (1972).

"Transfection" refers to the introduction of DNA into a host cell whether or not any coding sequences are ultimately expressed. Cells do not naturally take up DNA. Thus, a variety of technical "tricks" have been utilized to facilitate gene transfer. Numerous methods of transfection are known to the ordinarily skilled artisan, for example, $CaPO_4$ and electroporation. Transformation of the host cell is the indicia of successful transfection.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The polynucleotide of the present invention may be employed for producing a polypeptide by recombinant techniques. Thus, for example, the polynucleotide sequence may be included in any one of a variety of vectors or plasmids for expressing a polypeptide. Such vectors include chromosomal, nonchromosomal and synthetic DNA sequences, e.g., derivatives of SV40; bacterial plasmids; phage DNA'S; yeast plasmids; vectors derived from combinations of plasmids and phage DNAS, viral DNA such as vaccinia, adenovirus, fowl pox virus, and pseudorabies.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli,* lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein. As representative examples of appropriate hosts, there may be mentioned: bacterial cells, such as *E. coli, Salmonella typhimurium;* fungal cells, such as yeast; animal cells such as Cos-7 cells, CHO or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE-9 (Qiagen), pBs, phagescript, pD10, PsiXI74, pbluescript SK, pBsKS, PNH8A, PNE16A, PNH18A, PNH46A (Stratagene); Ptrc99a, PKK223-3, PKK233-3, PDR540, PRIT5 (Pharmacia). Eukaryotic: pWLneo, PSV2CAT, POG44, PXTI, pSG (Stratagene) PSVK3, PBPV, PMSG, PSVL (Pharmacia). Also, any other plasmids and vectors may be used as long as they are replicable and viable in the host.

Promoter regions can be selected from any desired gene using CAT (chloramphenicol acetyl transferase) vectors or other vectors with selectable markers. Two appropriate vectors are PKK232–8 and PCM7. Particular named bacterial promoters include lacl, lacz, T3, T7, gpt, lambda $P_R$ and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE, dextran mediated transfection, or electroporation (Davis, L., Dibner, M., Battey, I., *Basic Methods in Molecular Biology,* 1986).

The constructs in host cells can be used in a conventional manner to produce the gene product coded by the recombinant sequence. Alternatively, the encoded polypeptide can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., *Molecular Cloning,: A Laboratory Manual,* Second Edition, Cold Spring Harbor, N.Y., (1989), the disclosure of which is hereby incorporated by reference.

Transcription of a DNA encoding a polypeptide of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coil* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector PBR322 (ATCC 37017). Such commercial vectors include, for example, PKK223-3 (Pharmacia Fine Chemicals, Uppsala, Sweden) and GEM1 (Promega Biotec, Madison, Wis., USA). These PBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period. Cells are typically harvested by centrifugation, disrupted by physical or chemical means, and the resulting crude extract retained for further purification.

The repair proteins of the present invention may be recovered and purified from recombinant cell cultures by methods used heretofore, e.g. (Bende et al., Nucleic acid research, 19:1549–1555[1991]), including ammonium sulfate or ethanol precipitation, acid extraction, anion or cation or exchange chromatography, phosphocellulose chromatography, hydrophobic interaction chromatography, affinity chromatography (e.g., using DNA or nucleotides on a solid support), hydroxylapatite chromatography and lectin chromatography. Moreover, reverse-phase HPLC and chromatography using anti-mutL antibodies are useful for the purification of human mutL homologs.

Various mammalian cell culture systems can also be employed to express recombinant protein. Examples of mammalian expression systems include the COS-7 lines of monkey kidney fibroblasts, described by Gluzman, *Cell,* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Recombinant protein produced in bacterial culture is usually isolated by initial extraction from cell pellets, followed by one or more salting-outs, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

The polypeptide of the present invention may be a naturally purified product, or a product of chemical synthetic procedures, or produced by recombinant techniques from a prokaryotic or eukaryotic host (for example, by bacterial, yeast, higher plant, insect and mammalian cells in culture) of a polynucleotide sequence of the present invention. Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue (at position 1).

In addition to naturally occurring allelic forms of the polypeptide, the present invention also embraces analogs and fragments thereof. Thus, for example, one or more of the amino acid residues of the polypeptide may be replaced by conserved amino acid residues.

DNA mismatch can be generated during DNA replication and recombination. If these mutations were left unrepaired, mutated protein would result in altered or lost function of the normal protein. It has been found, for example, mutation on the human DNA mismatch repair gene hmsh2 is responsible for the hereditary nonpolyposis colon cancer (Fishel et al., Cell, 75:1027–1038[1993] and Leach et al., *Cell,* 75:1215–1225[19931]).

Each of the cDNA sequences identified herein or a portion thereof can be used in numerous ways as polynucleotide reagents. The sequences can be used as diagnostic probes for the presence of a specific mRNA in a particular cell type. In addition, these sequences can be used as diagnostic probes suitable for use in genetic linkage analysis (polymorphisms).

In accordance with a further aspect of the invention, there is provided a process for determining susceptibility to cancer, in particular, a hereditary cancer. Thus, a mutation in a human repair protein, which is a human homologue of mutL and in particular those described herein, indicates a susceptibility to cancer, and the nucleic acid sequences encoding such human homologues may be employed in an assay for ascertaining such susceptibility. Thus, for example, the assay may be employed to determine a mutation in a human DNA repair protein as herein described, such as a deletion, truncation, insertion, frame shift, etc., with such mutation being indicative of a susceptibility to cancer.

A mutation may be ascertained for example, by a DNA sequencing assay. Tissue samples including but not limited to blood samples are obtained from a human patient. The samples are processed by methods known in the art to capture the RNA. First strand cDNA is synthesized from the RNA samples by adding an oligonucleotide primer consisting of polythymidine residues which hybridize to the polyadenosine stretch present on the mRNA's. Reverse transcriptase and deoxynucleotides are added to allow synthesis of the first strand cDNA. Primer sequences are synthesized based on the DNA sequence of the DNA repair protein of the invention. The primer sequence is generally comprised of 15 to 30 and preferably from 18 to 25 consecutive bases of the human DNA repair gene. Table 1 sets forth an illustrative example of oligonucleotide primer sequences based on HMLH1. The primers are used in pairs (one "sense" strand and one "anti-sense") to amplify the cDNA from the patients by the PCR method such that three overlapping fragments of the patient's cDNA's for such protein are generated. Table 1 also shows a list of preferred primer sequence pairs. The overlapping fragments are then subjected to dideoxynucleotide sequencing using a set of primer sequences synthesized to correspond to the base pairs of the cDNA's at a point approximately every 200 base pairs throughout the gene. Table 2 lists representative examples of oligonucleotide primer sequences (sense and anti-sense) which may be used, and preferably the entire set of primer sequences are used for sequencing to determine where a mutation in the patient DNA repair protein may be. The primer sequences may be from 15 to 30 bases in length and are preferably between 18 and 25 bases in length. The sequence information determined from the patient is then compared to non-mutated sequences to determine if any mutations are present.

TABLE 1

Primer Sequences used to amplify gene region using PCR

| Name | Start Site and Arrangement | Sequence |
|---|---|---|
| 758 (SEQ ID NO:5, 1 to 20 of (SEQ ID NO:1) | sense-(-41) * | GTTGAACATCTAGACGTCTC |
| 1319 (SEQ ID NO:6, 49 to 67 of (SEQ ID NO:1) | sense-8 | TCGTGGCAGGGGTTATTCG |
| 1321 (SEQ ID NO:7, 660 to 678 of (SEQ ID NO:1) | sense-619 | CTACCCAATGCCTCAACCG |
| 1322 (SEQ ID NO:8, 718 to 739 of (SEQ ID NO:1) | sense-677 | GAGAACTGATAGAAATTGGATG |
| 1314 (SEQ ID NO:9, 1589 to 1606 of (SEQ ID NO:1) | sense-1548 | GGGACATGAGGTTCTCCG |
| 1323 (SEQ ID NO:10, 1634 to 1652 of (SEQ ID NO:1) | sense-1593 | GGGCTGTGTGAATCCTCAG |
| 773 (SEQ ID NO:11, complementary to 75 to 94 of (SEQ ID NO:1) | anti-53 | CGGTTCACCACTGTCTCGTC |
| 1313 (SEQ ID NO:12, complementary to 995 to 1012 of (SEQ ID NO:1) | anti-971 | TCCAGGATGCTCTCCTCG |
| 1320 (SEQ ID NO:13, complementary to 1079 to 1098 of (SEQ ID NO:1) | anti-1057 | CAAGTCCTGGTAGCAAAGTC |
| 1315 (SEQ ID NO:14, complementary to 1783 to 1801 of (SEQ ID NO:1) | anti-1760 | ATGGCAAGGTCAAAGAGCG |
| 1316 (SEQ ID NO:15, complementary to 1857 to 1878 of (SEQ ID NO:1) | anti-1837 | CAACAATGTATTCAGXAAGTCC |
| 1317 (SEQ ID NO:16, complementary to 2361 to 2381 of (SEQ ID NO:1) | anti-2340 | TTGATACAACACTTTGTATCG |
| 1318 (SEQ ID NO:17, complementary to 2436 to 2456 of (SEQ ID NO:1) | anti-2415 | GGAATACTATCAGAAGGCAAG |

\* Numbers correspond to location along nucleotide sequence of FIGS. 1A–F where ATG is number 1.
Preferred primer sequences pairs:
 758, 1313
1319, 1320
 660, 1909
 725, 1995
1680, 2536
1727, 2610

TABLE 2

Primer sequences Used to Sequence the Amplified Fragments

| Name | Number | Start Site and Arrangement | Sequence |
|---|---|---|---|
| 5282 | seq01 (SEQ ID NO:18, 418 to 438 of (SEQ ID NO:1) | sense-377* | ACAGAGCAAGTTACTCAGATG |
| 5283 | seq02 (SEQ ID NO:19, 593 to 613 of (SEQ ID NO:1) | sense-552 | AGTACACAATGCAGGCATTAG |
| 5284 | seq03 (SEQ ID NO:20, 945 to 965 of (SEQ ID NO:1) | sense-904 | AATGTGGATGTTAATGTGCAC |
| 5285 | seq04 (SEQ ID NO:21, 1137 to 1155 of (SEQ ID NO:1) | sense-1096 | CTGACCTCGTCTTCCTAC |
| 5286 | seq05 (SEQ ID NO:22, 1317 to 1335 of (SEQ ID NO:1) | sense-1276 | CAGCAAGATGAGGAGATGC |
| 5287 | seq06 (SEQ ID NO:23, 1478 to 1498 of (SEQ ID NO:1) | sense-1437 | GGAAATGGTGGAAGATGATTC |
| 5288 | seq07 (SEQ ID NO:24, 1686 to 1701 of (SEQ ID NO:1) | sense-1645 | CTTCTCAACACCAAGC |
| 5289 | seq08 (SEQ ID NO:25, 1936 to 1956 of (SEQ ID NO:1) | sense-1895 | GAAATTGATGAGGAAGGGAAC |
| 5295 | seq09 (SEQ ID NO:26, 1962 to 1983 of (SEQ ID NO:1) | sense-1921 | CTTCTGATTGACAACTATGTGC |
| 5294 | seq10 (SEQ ID NO:27, 2243 to 2264 of (SEQ ID NO:1) | sense-2202 | CACAGAAGATGGAAATATCCTG |
| 5293 | seq11 (SEQ ID NO:28, 2411 to 2430 of (SEQ ID NO:1) | sense-2370 | GTGTTGGTAGCACTTAAGAC |
| 5291 | seq12 (SEQ ID NO:29, complementary to 547 to 566 of (SEQ ID NO:1) | anti-525 | TTTCCCATATTCTTCACTTG |
| 5290 | seq13 (SEQ ID NO:30, complementary to 364 to 382 of (SEQ ID NO:1) | anti-341 | GTAACATGAGCCACATGGC |
| 5292 | seq14 (SEQ ID NO:31, complementary to 69 to 87 of (SEQ ID NO:1) | anti-46 | CCACTGTCTCGTCCAGCCG |

*Numbers correspond to location along nucleotide sequence of FIGS. 1A–F where ATG is number 1.

In another embodiment, the primer sequences from Table 2 could be used in the PCR method to amplify a mutated region. The region could be sequenced and used as a diagnostic to predict a predisposition to such mutated genes.

the polypeptide of the present invention may also be employed in accordance with the present invention by expression of such polypeptide in vivo, which is often referred to as "gene therapy."

Thus, for example, cells may be transduced with a polynucleotide (DNA or RNA) encoding the polypeptide ex vivo, with the transduced cells then being provided to a patient to be treated with the polypeptide. Such methods are well-known in the art. For example, cells may be transduced by procedures known in the art by use of a retroviral particle containing RNA encoding the polypeptide of the present invention.

Similarly, transduction of cells may be accomplished in vivo for expression of the polypeptide in vivo for example, by procedures known in the art. As known in the art, a producer cell for producing a retroviral particle containing RNA encoding the polypeptide of the present invention may be administered to a patient for transduction in vivo and expression of the polypeptide in vivo.

These and other methods for administering a polypeptide of the present invention by such methods should be apparent to those skilled in the art from the teachings of the present invention. For example, the expression vehicle for transducing cells may be other than a retroviral particle, for example, an adenovirus.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of cDNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clone from which the EST was derived, and the longer the better. For example, 2,000 bp is good, 4,000 is better, and more than 4,000 is probably not necessary to get good results a reasonable percentage of the time. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. (Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The protein, its fragments or other derivatives, or analogs thereof, or cells expressing them can be used as an immunogen to produce antibodies thereto. These antibodies can be, for example, polyclonal, monoclonal, chimeric, single chain, Fab fragments, or the product of an Fab expression library. Various procedures known in the art may be used for the production of polyclonal antibodies.

Antibodies generated against the polypeptide corresponding to a sequence of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide. Moreover, a panel of such antibodies, specific to a large number of polypeptides, can be used to identify and differentiate such tissue.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kohler et al., 1983, *Immunology Today* 4:72), and the EBV-hybridoma technique to produce human monoclonal antibodies (Cole, et al., 1985, in *Monoclonal Antibodies and Cancer Therapy*, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

The antibodies can be used in methods relating to the localization and activity of the protein sequences of the invention, e.g., for imaging these proteins, measuring levels thereof in appropriate physiological samples and the like.

The present invention will be further described with reference to the following examples, however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour or longer at 37° C. are ordinarily used, but may vary in accordance with the supplier's instructions. After digestion the reaction is electrophoresed directly on an agarose gel to isolate the desired fragment.

Size separation of the cleaved fragments is performed using a 0.8–2.0 percent polyagarose gel. (Maniatis)

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 $\mu$g of approximately equimolar amounts of the DNA fragments to be ligated.

EXAMPLE 1

Bacterial Expression of Human DNA Mismatch Repair Protein

The full length DNA sequence encoding for human DNA mismatch repair protein hmlh1 (ATCC #75649) is initially amplified using PCR oligonucleotide primers corresponding to the 5' and 3' end of the DNA sequence to synthesize insertion fragments. The 5' oligonucleotide primer has the sequence 5'-CGGGATCCATGTCGTTCGTGGCAGGG-3' (SEQ ID NO:32), contains a BamHI restriction enzyme site followed by 18 nucleotides of HMLH1 coding sequence following the initiation codon; the 3' sequence 5'-GCTCTAGATTAACACCTCTCAAAGAC-3' (SEQ ID NO:33) contains complementary sequences to XbaI site and is at the end of the gene. The restriction enzyme sites correspond to the restriction enzyme sites on the bacterial expression vector pQE-9. (Qiagen, Inc. 9259 Eton Avenue, Chatsworth, Calif., 91311) The plasmid vector encodes antibiotic resistance (Amp'), a bacterial origin of replication (ori), an IPTG-regulatable promoter/operator (P/O), a ribosome binding site (RBS), a 6-histidine tag (6-His) and restriction enzyme cloning sites. The pQE-9 vector was digested with BamHI and XbaI and the insertion fragments were then ligated into the pQE-9 vector maintaining the reading frame initiated at the bacterial RBS. The ligation mixture was then used to transform the E. coli strain GW3733 (k-12, argE3 hisG4, LeuB6 proA2 thr-1 ara-1 rpsL31 supE44 tsx-33 mut1218::Tn10). Transformants are identified by their ability to grow on LB plates containing Amp.

Clones containing the desired constructs were grown overnight in liquid culture in LB media supplemented with Amp (100 mg/ml). The O/N culture issued to inoculate a large culture at a ratio of 1:100 to 1:250. The cells were grown to an optical density at 600 nm ($0.0^{600}$) of between 0.4 and 0.6. IPTG ("Isopropyl-B-D-thiogalacto pyranoside") is then added to a final concentration of 1 mM. IPTG induces gene expression by inactivating the LacI repressor. Cells are grown an extra 2-4 hours and then harvested by centrifugation. Expression of human mut L homolog 1 is tested by solubilizing a portion of the E. coli and analyzing on a SDS polyacrylamide gel.

Purification of the protein is accomplished by utilization of the hexa-histidine sequence. Following induction of the E. coli pellet is solubilized in 6M guanidine HCl. The protein is purified using a Nickel-Chelate resin column having a high affinity for the hexa-histidine sequence. (Hachule, E. et al., *Genetic Engineering, Principles and Methods*, 12:87–98, Plenum Press, NY (1990). The column was washed and the protein is eluted at a pH of 5.0. Protein renaturation is accomplished by removing the guanidine HCl from the protein isolate by any one of several protocols. (Jaenicke, R. et al., *Protein Structure-A Practical Approach*. IRL Press, New York (1990). The purified protein is analyzed by SDS-PAGE.

EXAMPLE 2
Spontaneous Mutation Assay for Detection of the Expression of Human mutL and Complementation to the E. coli mut1

The pQE9hmlh1 /GW3733 transformants were subjected to the spontaneous mutation assay. The plasmid vector pQE9 was also transformed to AB1157 (k-12, argE3 hisG4,LeuB6 proA2 thr-1 ara-1 rpsL31 supE44 tsx-33) and GW3733 to use as the positive and negative control respectively.

Fifteen 2 ml cultures, inoculated with approximately 100 to 1000 E.coli, were grown $2 \times 10^8$ cells per ml in LB ampicillin medium at 37° C. ten microliters of each culture were diluted and plated on the LB ampicillin plates to measure the number of viable cells. The rest of the cells from each culture were then concentrated in saline and plated on minimal plates lacking of arginine to measure reversion of $Arg^+$. The mean number of mutations per culture (m) was calculated from the median number (r) of mutants per distribution, according to the equation $(r/m)-\ln(m)=1.24$ (Lea et al., J. Genetics 49:264–285[1949]). Mutation rates per generation were recorded as m/N, with N representing the average number of cells per culture.

| Strain | Mutation rate (Mutations/cell/generation) |
|---|---|
| AB1157 / pQE9 | $0.22 \times 10^{-9}$ |
| Gw3733 / pQE9 | $7.5 \times 10^{-9}$ |
| GW3733 /pQE9hmlhl | $0.37 \times 10^{-9}$ |

The functional complementation result showed that the human mutL can fully rescue the E.coli mutL mutator phenotype, suggesting that the human mutL can not only express but also function in bacteria.

EXAMPLE 3
Chromosomal Mapping of the Human Mut L Homolog1

An oligonucleotide primer set was designed according to the sequence at the 5' end of the cDNA for HMLH1. This primer set would span a 94 bp segment. This primer set was used in a polymerase chain reaction under the following set of conditions:

30 seconds, 95 degrees C.
1 minute, 56 degrees C.
1 minute, 70 degrees C.

This cycle was repeated 32 times followed by one 5 minute cycle at 70 degrees C. Human, mouse, and hamster DNA were used as template in addition to a somatic cell hybrid panel (Bios, Inc). The reactions were analyzed on either 8% polyacrylamide gels or 3.5 % agarose gels. A 94 base pair band was observed in the human genomic DNA sample and in the somatic cell hybrid sample corresponding to chromosome 3. In addition, using various other somatic cell hybrid genomic DNA, the human Mut L homolog HMLH1 was localized to chromosome 3p.

Numerous modifications and variations of the present invention are possible in light of the above teachings and therefore within the scope of the appended claims, the invention may be practised otherwise than as specifically described herein.

We claim:

1. An isolated polynucleotide comprising a nucleic acid sequence selected from the group consisting of:

(a) a nucleic acid sequence encoding amino acids +1 to +756 of SEQ ID NO:2;

(b) a nucleic acid sequence encoding the amino acid sequence encoded by the cDNA contained in ATCC Deposit No. 75649; and (c) a nucleic acid sequence encoding a polypeptide fragment of SEQ ID NO:2 or a polypeptide fragment encoded by the cDNA contained in ATCC Deposit No. 75649, wherein said fragment has mismatch repair activity.

2. The isolated polynucleotide of claim 1, wherein said nucleic acid sequence is (a).

3. The isolated polynucleotide of claim 2, comprising nucleotides +42 to +2309 of SEQ ID NO: 1.

4. An isolated polynucleotide complementary to the polynucleotide of claim 2.

5. The isolated polynucleotide of claim 2 further comprising a heterologous polynucleotide.

6. The isolated polynucleotide of claim 5, wherein the heterologous polynucleotide encodes a heterologous polypeptide.

7. A vector comprising the polynucleotide of claim 2.

8. A host cell comprising the polynucleotide of claim 2 operably associated with a heterologous regulatory sequence.

9. A method of producing a polypeptide comprising:

(a) culturing the host cell of claim 8 under conditions such that the polypeptide is expressed; and (b) recovering said polypeptide.

10. A composition comprising the isolated polynucleotide of claim 2 and a carrier.

11. The isolated polynucleotide of claim 1, wherein said nucleic acid sequence is (b).

12. An isolated polynucleotide complementary to the polynucleotide of claim 11.

13. The isolated polynucleotide of claim 11 further comprising a heterologous polynucleotide.

14. The isolated polynucleotide of claim 13, wherein the heterologous polynucleotide encodes a heterologous polypeptide.

15. A vector comprising the polynucleotide of claim 11.

16. A host cell comprising the polynucleotide of claim 11 operably associated with a heterologous regulatory sequence.

17. A method of producing a polypeptide comprising:

(a) culturing the host cell of claim 16 under conditions such that the polypeptide is expressed; and (b) recovering said polypeptide.

18. A composition comprising the isolated polynucleotide of claim 11 and a carrier.

19. The isolated polynucleotide of claim 1, wherein said nucleic acid sequence is (c).

20. An isolated polynucleotide complementary to the polynucleotide of claim 19.

21. The isolated polynucleotide of claim 19 further comprising a heterologous polynucleotide.

22. The isolated polynucleotide of claim 21, wherein the heterologous polynucleotide encodes a heterologous polypeptide.

23. A vector comprising the polynucleotide of claim 19.

24. A host cell comprising the polynucleotide of claim 19 operably associated with a heterologous regulatory sequence.

25. A method of producing a polypeptide comprising:
   (a) culturing the host cell of claim 24 under conditions such that the polypeptide is expressed; and
   (b) recovering said polypeptide.

26. A composition comprising the isolated polynucleotide of claim 19 and carrier.

* * * * *

UNITED STATES PATENT AND TRADEMARK OFFICE
CERTIFICATE OF CORRECTION

PATENT NO. : 6,482,606 B1
DATED : November 19, 2002
INVENTOR(S) : Adams et al.

It is certified that error appears in the above-identified patent and that said Letters Patent is hereby corrected as shown below:

<u>Title page,</u>
Item [56], References Cited, OTHER PUBLICATIONS,
"Auffray et al." reference, please change "Berkank" to read -- Genbank -- and "236291" to read -- Z36291 --;
"Okubo et al." reference, please change "HumosisA10) (Dec. 1," to read -- HUM0S15A10) (Dec. 2, --;
"Bionner, C.E. et al." reference, please change "LmLH1" to read -- hMLH1 --;

Please insert the following references:
-- Prolla et al., "Dual Requirement in Yeast DNA Mismatch Repair for MLH1 and PMS1, two homologs of bacterial mutL Gene," Molecular and Cellular Biology 14(1): 407-415, (1994).
New et al., "The yeast gene MSH3 defines a new class of eukaryotic MutS homologues," Mol. Gen. Genet. 239:97-108, (1993). --

<u>Column 3,</u>
Line 14, please insert the following address:
-- American Type Culture Collection, 10801 University Boulevard, Manassas, VA 20110-2209 --

Signed and Sealed this

Fifteenth Day of July, 2003

JAMES E. ROGAN
*Director of the United States Patent and Trademark Office*